(12) United States Patent
Hirabayashi et al.

(10) Patent No.: US 6,904,302 B2
(45) Date of Patent: Jun. 7, 2005

(54) OPTICAL SYSTEM FOR MEASURING METABOLISM IN A BODY

(75) Inventors: Yukiko Hirabayashi, Kokubunji (JP); Tsuyoshi Yamamoto, Kawagoe (JP)

(73) Assignees: Hitachi, Ltd., Tokyo (JP); Hitachi Medical Corporation, Tokyo (JP)

( * ) Notice: Subject to any disclaimer, the term of this patent is extended or adjusted under 35 U.S.C. 154(b) by 119 days.

(21) Appl. No.: 10/639,439

(22) Filed: Aug. 13, 2003

(65) Prior Publication Data

US 2004/0077935 A1 Apr. 22, 2004

(30) Foreign Application Priority Data

Oct. 7, 2002 (JP) ....................................... 2002-293153

(51) Int. Cl.⁷ ................................................ A61B 5/00
(52) U.S. Cl. ....................................... 600/344; 600/340
(58) Field of Search ................................ 600/310, 322, 600/323, 340, 344

(56) References Cited

U.S. PATENT DOCUMENTS

| | | | | |
|---|---|---|---|---|
| 5,803,909 A | * | 9/1998 | Maki et al. ................. | 600/310 |
| 5,853,370 A | * | 12/1998 | Chance et al. ............. | 600/323 |
| 6,611,698 B1 | * | 8/2003 | Yamashita et al. .......... | 600/340 |

FOREIGN PATENT DOCUMENTS

| | | |
|---|---|---|
| EP | 1 407 711 A1 | 8/2003 |
| JP | 2002-502653 | 2/1999 |
| JP | 2001-286449 | 4/2000 |
| JP | 2002-011012 | 6/2000 |
| JP | 2002-143169 | 11/2000 |
| WO | WO 99/40841 | 2/1999 |

OTHER PUBLICATIONS

Atsushi Maki, Yuichi Yamashita, Yoshitoshi Ito, Eiju Watanabe, Yoshiaki Mayanagi and Hideaki Koizumi, "Spatial and Temporal Analysis of Human Motor Activity Using Noninvasive NIR Topography", Medical Physics, vol. 22, No. 12, Dec. 1995, pp. 1997–2005.

Tsuyoshi Yamamoto, Yuichi Yamashita, Hiroshi Yoshizawa, Atsushi Maki, Makato Iwata, Eiju Watanabe, and Hideaki Koizuma, "Non–invasive Measurement of Language Function By Using Optical Topography", part of the SPIE Conference on Optical Tomography and Spectroscopy of Tissue III, vol. 3597, Jan. 1999, pp. 230–237.

* cited by examiner

*Primary Examiner*—Eric F. Winakur
(74) *Attorney, Agent, or Firm*—Reed Smith LLP; Stanley P. Fisher, Esq.; Juan Carlos A. Marquez, Esq.

(57) ABSTRACT

Irradiated points and light receiving points are arranged such that sampling points are arranged over an entire spherical head with no vacant space. The sampling points are arranged to cover the entire spherical head by combining a plurality of rhombic shells and inverting the respective positions of irradiated points and light receiving points in the adjacent shells. As a result, a whole brain probe capable of covering the entire head is provided to allow an image of the whole brain to be viewed as a single image.

8 Claims, 13 Drawing Sheets

OPTICAL SYSTEM FOR MEASURING METABOLISM IN A BODY

FIELD OF THE INVENTION

The present invention relates to an optical system for measuring, by using light, the concentration or variations in the concentration of a metabolite in a living body and more particularly, to a probe for measuring the concentration of a metabolite in a head.

BACKGROUND OF THE INVENTION

Figure 1:
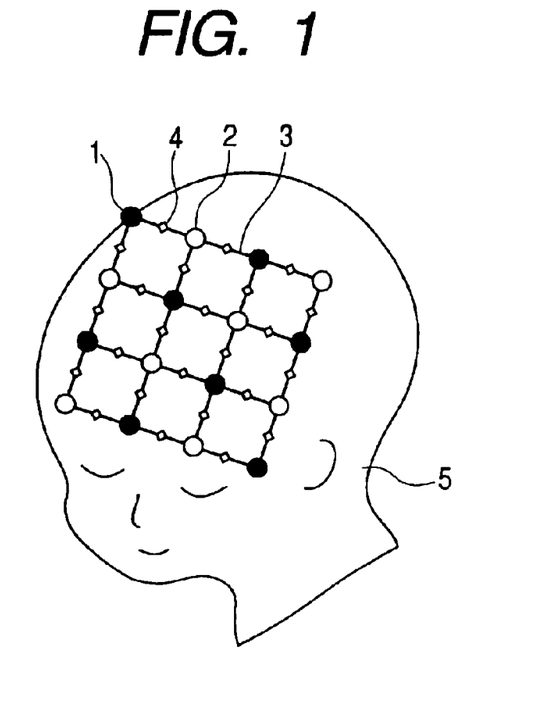
FIG. 1 is a view showing an example of conventional probes for an optical topography system.

A technology (optical topography system) which measures variations in blood volume in a cerebral cortex with brain activity at multiple points and displays the variations in blood volume as a dynamic image or a static image has already been disclosed in Medical Physics, vol. 22, No. 12 pp. 1997–2005 (1995) (Atsushi Maki, Yuichi Yamashita, Yoshitoshi Ito, Eijyu Watanabe, Yoshiaki Mayanagi, and Hideki Koizumi, "Spatial and temporal analysis of human motor activity"), and in "Non-invasive measurement of language function by using optical topography", Proceedings of SPIE, vol. 3597, pp. 230–237 (Tsuyoshi Yamamoto, Yuichi Yamashita, Hiroshi Yoshizawa, Atsushi Maki, Makoto Iwata, Eiju Watanabe, Hideaki Koizumi). In these papers, probes in an arrangement as shown in FIG. 1 are used. Eight irradiated points 1 to which optical fibers for incident lights are connected and eight light receiving points 2 to which optical fibers for detecting light are connected are alternately arranged on a shell 3 configured as a tetragonal lattice with 30-mm spacings. Substantially middle points between the irradiated points and the light receiving points are designated as sampling points 4. It follows therefore that the total of twenty-four sampling points are present with about 21-mm spacings over a region of 90 mm×90 mm. In the foregoing optical topography system, nearly uniform distances (which are 30 mm in FIG. 1) should be provided between the irradiated points and the light receiving points with the sampling points interposed therebetween.

Since it is difficult to bring a probe configured as a tetragonal lattice as described above into close contact with an entire spherical head, the following inventions have already been disclosed.

Probes for an optical topography system having branched portions extending from a coupling shaft to fit to the configuration of a head are disclosed in Japanese Laid-Open Patent Publication No. 2001-286449.

Probes for an optical topography system arranged in a lattice configuration which are characterized in that the coupler for the probes rotate and holders for holding the individual probes have elasticity are disclosed in Japanese Laid-Open Patent Publication No. 2002-143169.

Probes which cover an entire head by filling a plurality of regions of the head with tetragonal lattices and filling the gaps therebetween with polygons are disclosed in Japanese Laid-Open Patent Publication No. 2002-11012.

On the other hand, a system for non-invasively measuring the brain tissue of a subject by geometrically arranging probes on the head of the subject is disclosed in Domestic-Phase PCT Patent Application No. 2002-502653.

However, the optical topography systems and probes described above have the following problems.

Since the probes described above partially cover a head or cover the entire head by dividing the head into regions and placing a probe set on each of the regions, it has been impossible to represent the metabolic state of an entire brain as a single continuous image. In the conventional probe arrangement configured as a tetragonal lattice, it has been difficult to cover at least the upper half of a head by arranging a plurality of irradiated/light receiving point sets, while maintaining nearly uniform distances between the irradiated/light receiving points.

SUMMARY OF THE INVENTION

The present invention has been achieved in view of the foregoing problems and it is therefore an object to the present invention to display at least the upper half of a head corresponding to a brain as a single image through close contact with the spherical head.

To solve the foregoing problems, the following solutions are provided.

Figure 2:
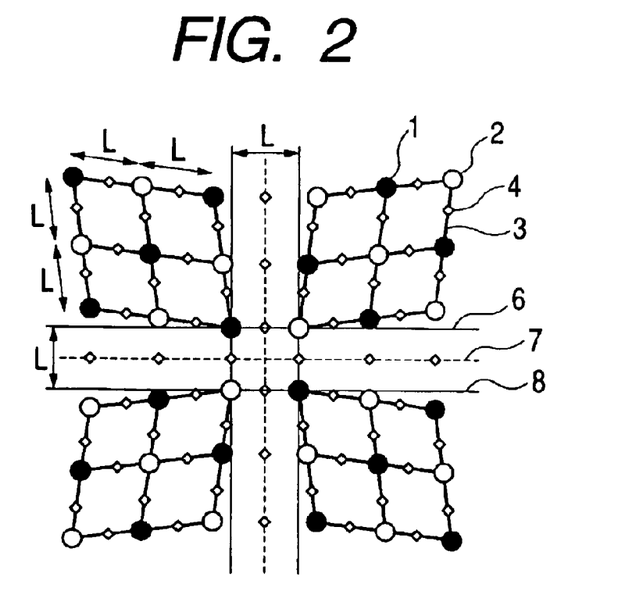
FIG. 2 is a view showing the arrangement of the shells of probes for an optical topography system according to an embodiment of the present invention that have been developed in a plane.
Figure 3A:
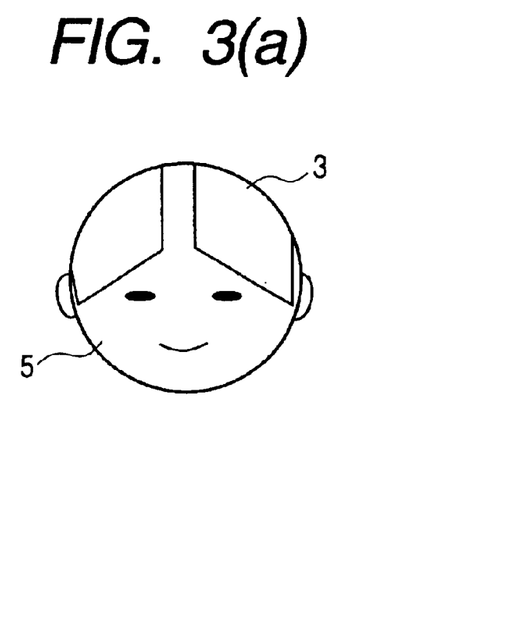
FIGS. 3A and 3B are views each showing the arrangement of the shells when the probes according to the foregoing embodiment are attached.
Figure 3B:
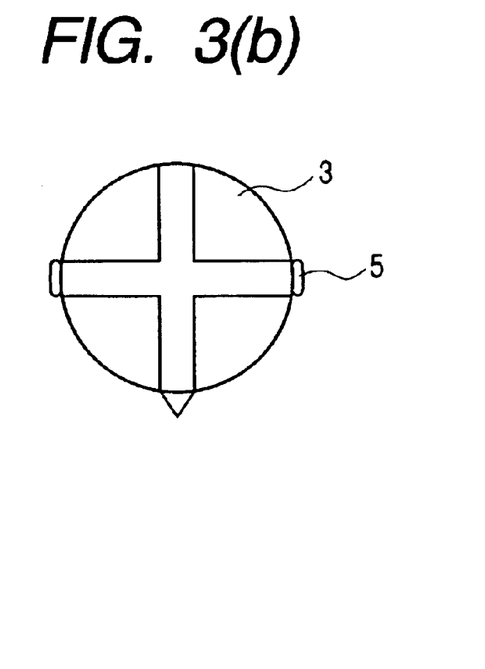

Since a tetragonal lattice does not conform to a spherical configuration, the tetragonal lattice is obliquely deformed such that a rhombic shell is used (FIG. 2). Moreover, a plurality of rhombi are arranged to have their respective acute angles located at a parietal region such that the respective edges of the adjacent rhombi are equidistant from each other (FIGS. 3A and 3B). Furthermore, the positions of the respective irradiated/light receiving points of the adjacent rhombic shells are inverted and the distances between the respective edges of the adjacent rhombic shells are adjusted to be nearly equal to the distances between the irradiated points and the light receiving points. This allows the sampling points to be provided even between the adjacent rhombi (FIG. 2).

Figure 4:
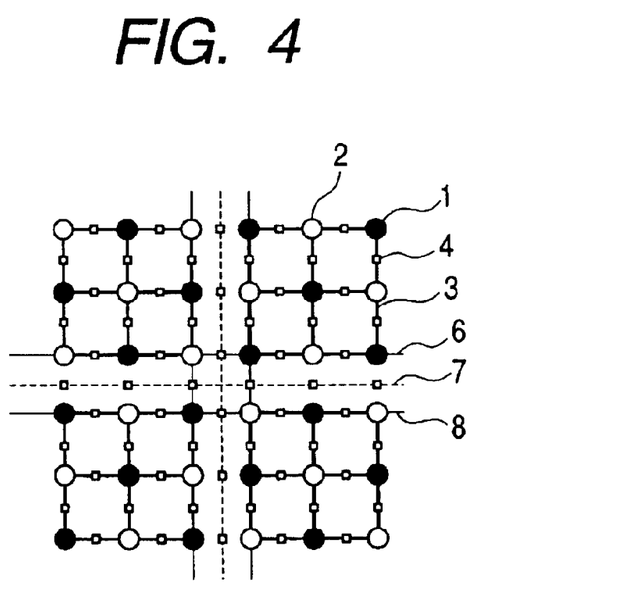
FIG. 4 is a plan view showing the corrected arrangement of the light transmitting/receiving portions of the actual shells of the probes according to the foregoing embodiment.
Figure 5:
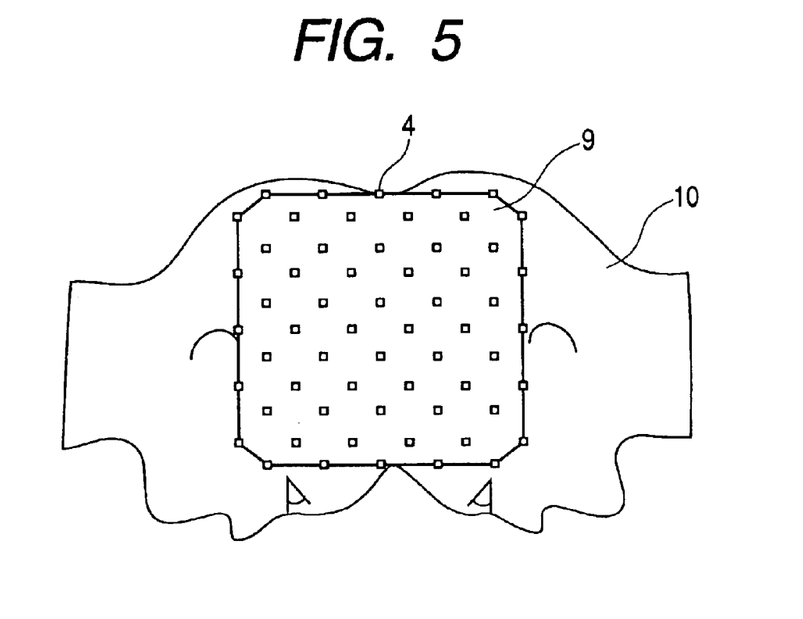
FIG. 5 is a view showing the display of an optical topography image obtained according to the foregoing embodiment.

If correction is made with respect to the sampling points arranged in the rhombic configuration thus obtained to form a tetragonal lattice (FIG. 4), it becomes possible to display the state of blood flows over the entire brain as a single 2D image (FIG. 5).

DESCRIPTION OF THE PREFERRED EMBODIMENTS

The embodiments of the present invention will be described herein below.

FIG. 1 is a view showing a conventional arrangement of probes. Irradiated points 1 and light receiving points 2 are arranged in nearly equi-spaced relation on a shell 3 configured as a tetragonal lattice. The shell 3 is attached to the head of a subject 5. Light for measurement emitted from a lamp, a light-emitting diode, a semiconductor laser, or the like passes through an optical fiber for incidence to be incident on the subject 5 from each of the irradiated points 1. The light propagated through a cerebral cortex portion in the head of the subject 5 passes through an optical fiber for detection attached to each of the light receiving points 2 to be transmitted to a light detector such as a photodiode or a photoelectron multiplier tube and detected. Since the intensity of the detected light fluctuates depending on the state of blood flows in the cerebral cortex, an increase and a decrease in the blood in the cerebral cortex through which the light has been propagated can be measured. Although a detect signal reflects information on blood flows throughout all the portions through which the light has been propagated, it is possible to designate substantially middle points between the irradiated points 1 and the light receiving points 2 as sampling points 4 and designate, for the sake of convenience, measured signal values as information on blood flows at the sampling points 4. From information on blood flows at a plurality of sampling points determined by the adjacent pairs of irradiated points and light receiving points, a blood flow distribution image can be obtained.

FIG. 2 is a developed view of the arrangement of the irradiated points and light receiving points of probes according to an embodiment of the present invention. Four rhombic shells 3 obtained by obliquely deforming tetragonal lattices are arranged. On the shells 3, the irradiated points 1 and the light receiving points 2 are arranged alternately. As a result, four partial arrays in each of which the irradiating portions of a light irradiator and the light receiving portions of a light detector are alternately arranged in a rhombic lattice configuration obtained by obliquely deforming a tetragonal configuration are combined to form an overall arrangement. In the adjacent shells, the irradiated points 1 and the light receiving points 2 are arranged such that the respective positions thereof are inverted. If the probes are actually placed on a head, the edges of the shells 3 are located in superimposed relation on correction lines 6 and 8 since the head is spherical. If the distance between the shells is adjusted to substantially the same value as the length L of a line composing the rhombic lattice, the region located between the irradiated point and the light receiving point belonging to the adjacent shells can also be measured in the same manner as on the same single shell so that the sampling points 3 are formed also on the middle line 7 between the shells. Accordingly, the four 3×3 shells provides a 6×6 image of the entire head.

The inner angles of the rhombi may be changed in accordance with the size of the head. Rhombi having small inner angles are used in the case of measuring a small head and rhombic shells having larger inner angles are used in the case of measuring a large head. Although the length of a connecting portion between the irradiated/light receiving points is not elongated, if the shells 3 are formed of an elastic material such that the apical angles of the rhombi are variable, shells capable of fitting to the head are realized. For example, a material such as a silicone rubber with low elasticity may be used. The shells 3 may be net-like shells formed only of the coupling members indicated by the bold lines in FIG. 2 or may be sheet-like shells. Alternatively, the shells 3 may have a structure obtained by combining thin sheets and coupling members which maintain the distances between the irradiated points and the light receiving points. In an actual situation, the coupling members couple optical fiber fixing sockets, the detailed structure of which will be described later.

FIGS. 3A and 3B show probes using four of the rhombic shells 3 described above which are attached to the subject 5, of which FIG. 3A is a front view of the subject and FIG. 3B shows the probes when viewed from above the parietal region of the subject. The apexes of the rhombic shells 3 are disposed to surround the parietal region so that the shells 3 are located on the left and right frontal regions and on the left and right occipital regions. If the distances between the shells are held nearly uniform, the apex portions may also be disposed to surround a portion other than the parietal region. Alternatively, the shells may also be disposed at the frontal region, the right temporal region, the left temporal region, and the occiptal region. It will easily be appreciated that the shells may be disposed at any positions provided that the distance between the shells are held nearly uniform.

If an image is displayed as it is in a developed view of rhombi as shown in FIG. 2, the image is hard to be viewed as a plan image so that correction is made to provide an arrangement as shown in FIG. 4. If the correction is made to change the rhombi into a tetragonal lattice, the tetragonal lattices are arranged along the correction lines 6 and 8 in a plane so that the entire head is displayed as a single plan image.

FIG. 5 shows an example of the display of an image thus corrected. An image 9 obtained by making correction to change the rhombi into the tetragonal lattice, connecting the plurality of sampling points 4 through correction to each other, and performing interpolation therebetween is disposed in superimposing relation on a head image 10 that has been corrected similarly and deformed. Since the head image has also been corrected and deformed similarly to the irradiated/light receiving points, positions with signal changes on a measurement image can more easily be associated with the positions on the head. As the image disposed in superimposing relation on the measurement image, a developed view of a brain that has been corrected similarly may also be used. Besides the correction method which changes the rhombi into the tetragonal lattice, correction may also be made in an easy-to-view form. It will easily be appreciated that 3D display may also be performed without making correction.

Figure 6:
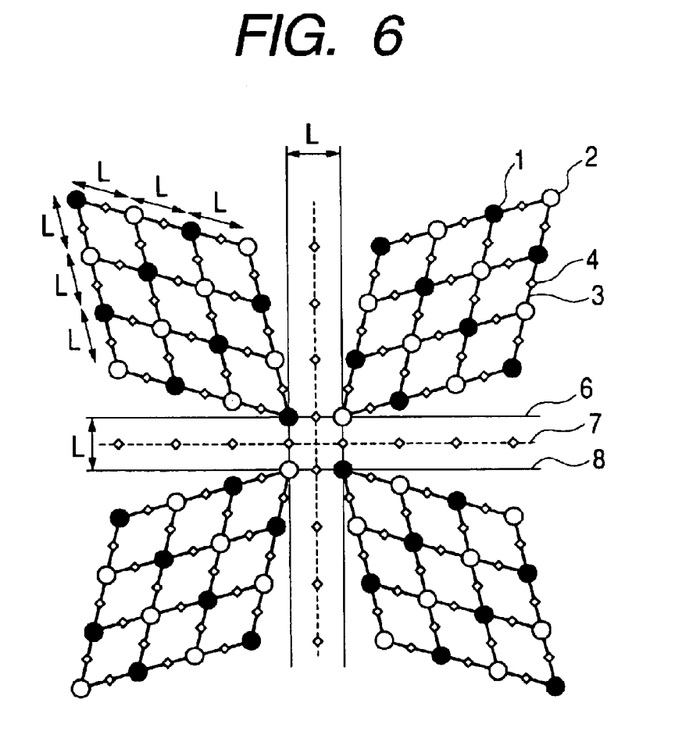
FIG. 6 is a view showing the arrangement of the shells of probes according to another embodiment that have been developed in a plane.

FIG. 6 shows another embodiment of the arrangement of probes. A 8×8 image is obtainable by using four 4×4 shells. The number of the shells need not necessarily be 4. However, it is necessary to use an even number of shells to measure each of the regions located between the shells.

Figure 7:
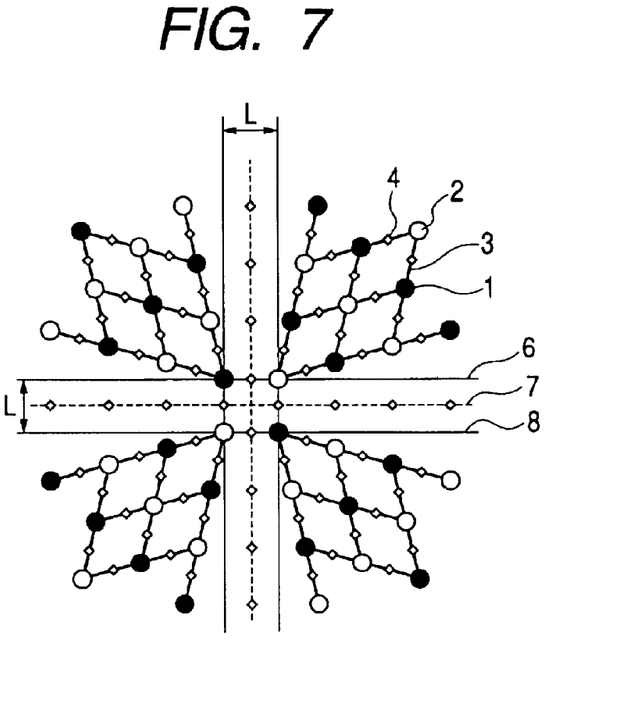
FIG. 7 is a view showing the arrangement of the shells of probes according to still another embodiment that have been developed in a plane.

FIG. 7 shows still another embodiment of the arrangement of probes. Measurement is basically for obtaining a 8×8 image by using four 4×4 shells but five irradiated/light receiving points arranged, i.e., these points in the vicinity of the eyes and the neck are removed from each of the shells. In short, an optical fiber is not connected to each of the five points. By thus keeping some of the points from being connected to optical fibers, a region close to the eyes is kept from irradiation so that safe measurement is ensured.

If there is no input signal to one of the light receiving points 2 by trouble or the like, not by intentionally keeping the point from being connected to an optical fiber as described above or if the S/N ratio of a signal value is inferior, it is also possible to estimate the signal to the light receiving point 2 by using a signal value or values to a single or plurality of light receiving points in the vicinity thereof without using the signal to the light receiving point 2 in question and thereby interpolate an image in the region corresponding to the portion.

Figure 8:
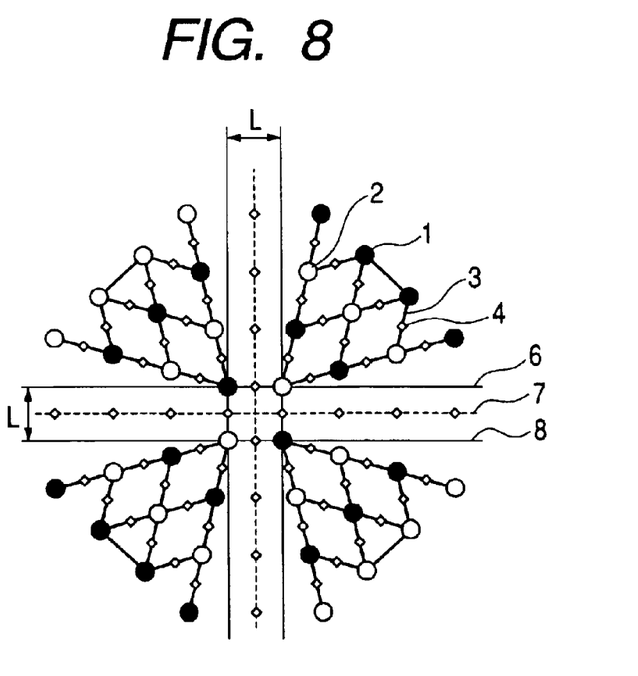
FIG. 8 is a view showing the arrangement of the shells of probes according to yet another embodiment that have been developed in a plane.

FIG. 8 also shows an embodiment of the arrangement of probes. In the present embodiment also, measurement is for obtaining a 8×8 image by using four 4×4 shells but six irradiated/light receiving points are removed from each of the shells.

Figure 9:
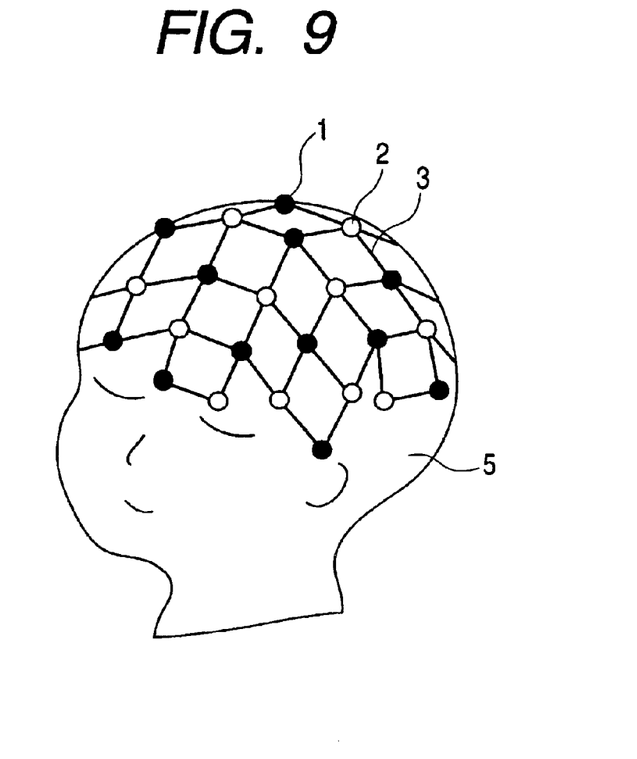
FIG. 9 is a view showing the arrangement of the light transmitting/receiving portions when the probes shown in FIG. 7 are attached.

FIG. 9 shows the case where the probes in the arrangement of FIG. 7 are attached to the head of the subject 5. Since the irradiated/light receiving points in the vicinity of the eyes are removed, safe measurement is performed. In the description given thus far, probes are formed by arranging four rhombic shells on the head of the subject. In an actual situation, however, finished probes need not necessarily have a structure that can be decomposed into the shells. Although the coupling members are depicted to exist only within each of the shells in the developed views of FIGS. 2, 6, and 7, this is for easy understanding of the structure. As shown in FIG. 9, the shells have been coupled from the beginning with similar coupling members in the finished probes. It is to be noted that the subsequent developed views also have similar omission.

Figure 10:
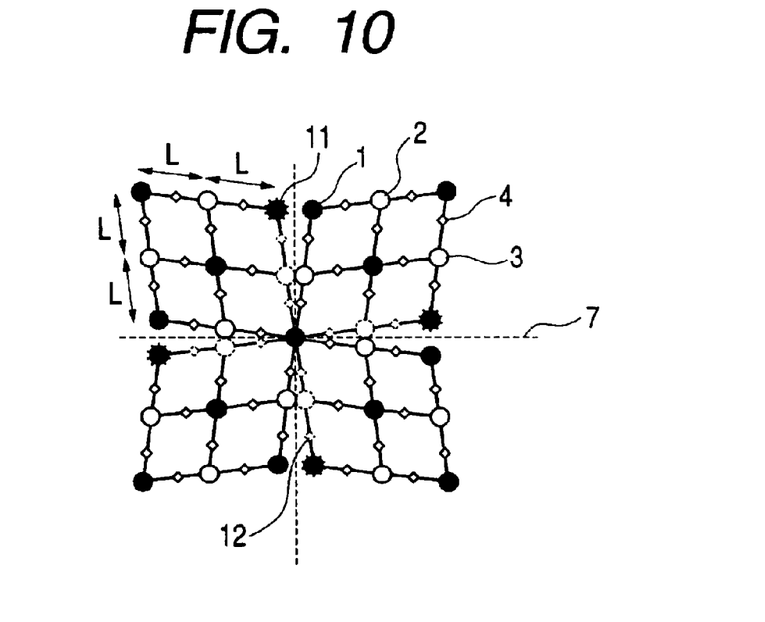
FIG. 10 is a view showing the arrangement of the shells of probes according to still another embodiment that have been developed in a plane.

FIG. 10 shows still another embodiment of the arrangement of probes. In this case, the individual shells 3 are not arranged in mutually spaced apart relation but are arranged such that the respective irradiated points and respective light receiving points of the adjacent shells are in overlapping relation. It follows therefore that one irradiation point and one light receiving point serve as the respective irradiated points and light receiving points of the adjacent two shells. Specifically, the irradiated point 1 indicated by the solid circle in FIG. 10 also serves as the overlapping irradiated point 11 indicated by the dotted circle on the adjacent shell.

Figure 11:
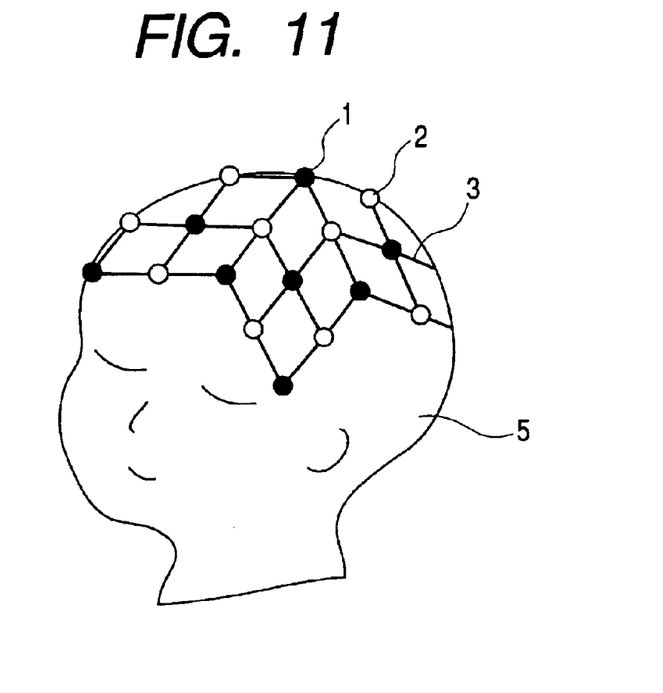
FIG. 11 is a view showing the arrangement of the light transmitting/receiving portions when the probes shown in FIG. 10 are attached.

FIG. 11 shows an example of the attachment of the probes in the arrangement of FIG. 10. The irradiated points and light receiving points of the adjacent shells are shared.

Figure 12:
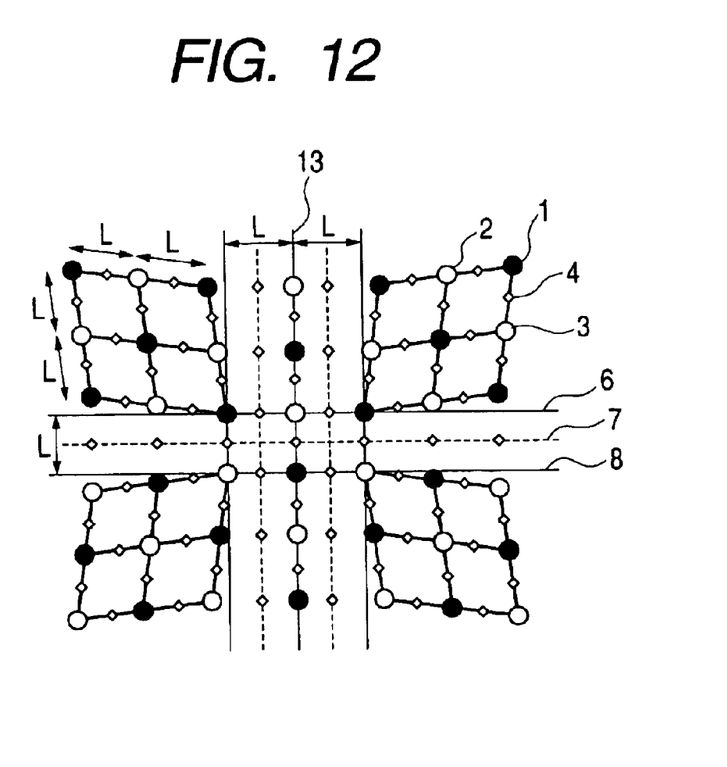
FIG. 12 is a view showing the arrangement of the shells of probes according to yet another embodiment that have been developed in a plane.

FIG. 12 shows yet another embodiment of the arrangement of probes. In the present embodiment, the distance between adjacent shells is adjusted to 2L and irradiated points 1 and light receiving points 2 are aligned on a substantially middle line 13 between the adjacent shells. It may also be said that a structure in which rhombic shells on the left and right hands are coupled with a shell in a tetragonal arrangement is formed. The arrangement is suitable for use on a subject having a head which is oblong in a front-to-rear direction. Since the density of sampling points 3 is higher in the vicinity of the parietal region, the effect of increased resolution in the vicinity of the parietal region is also achieved.

Figure 13:
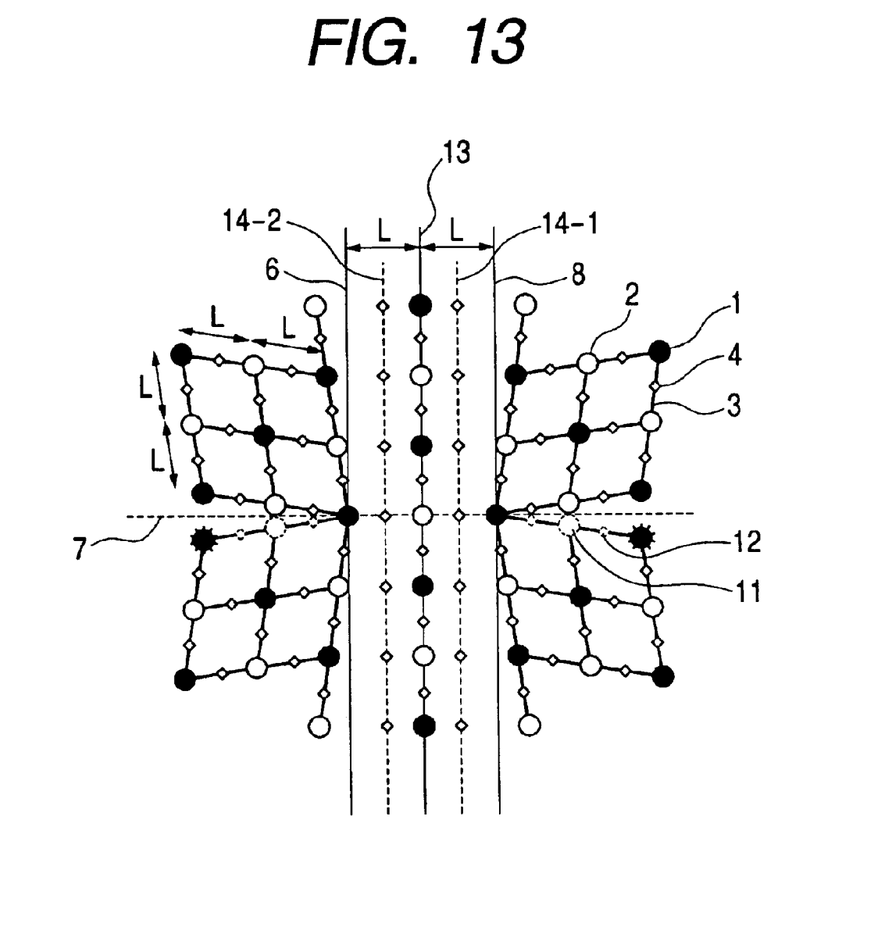
FIG. 13 is a view showing the arrangement of the shells of probes according to still another embodiment that have been developed in a plane.

FIG. 13 shows another embodiment of the arrangement in which irradiated points and light receiving points are aligned on a line 13 located between the adjacent shells, similarly to FIG. 12. The arrangement of shells is more fittable to a head which is oblong in the front-to-rear direction.

Figure 14A:
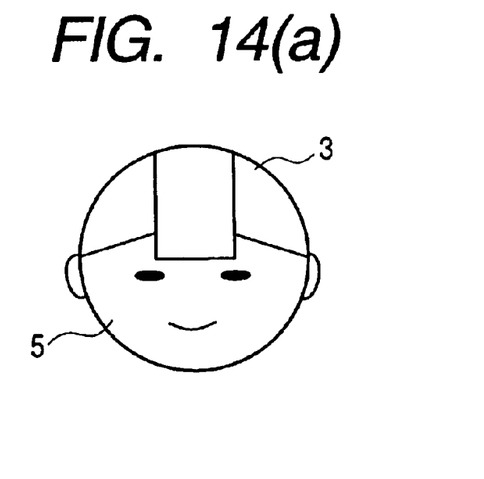
FIGS. 14A and 14B are views each showing the arrangement of the shells when the probes shown in FIG. 13 are attached.
Figure 14B:
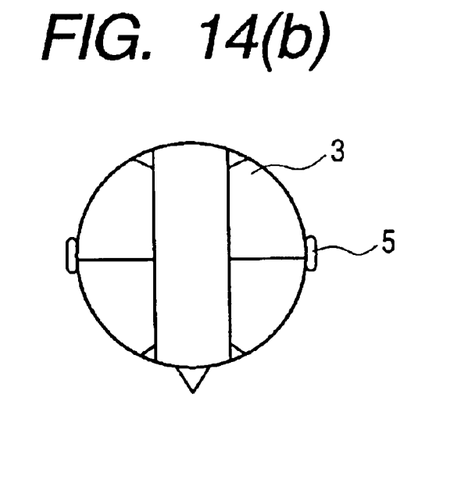

FIGS. 14A and 14B show the arrangement of the shells when probes in the arrangement of FIG. 13 are attached to a subject, of which FIG. 14A is a front view of the subject and FIG. 14B shows the probes when viewed from above the parietal region of the subject. The rhombic shells 3 are attached to be positioned on the temporal region of the subject 5.

Figure 15:
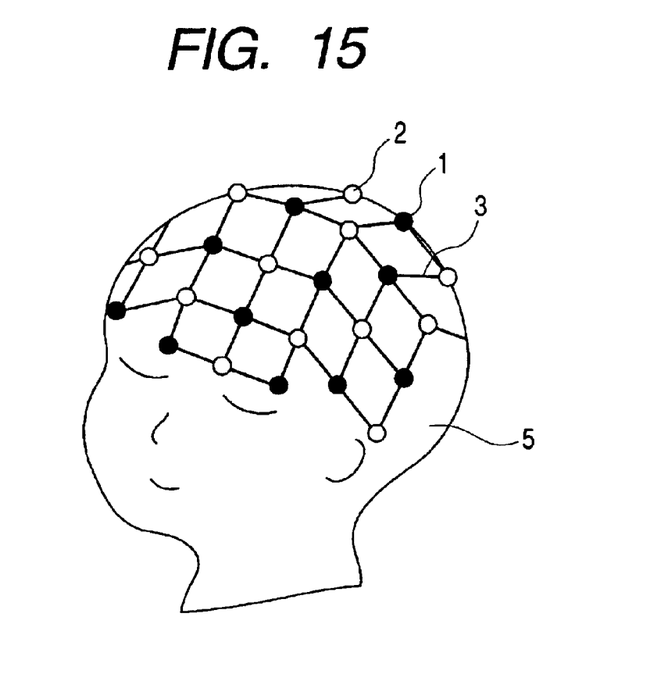
FIG. 15 is a view showing the arrangement of the light transmitting/receiving portions when the probes shown in FIG. 13 are attached.

FIG. 15 is a view similarly showing the probes in the arrangement of FIG. 13 when they are attached to a subject.

Figure 16:
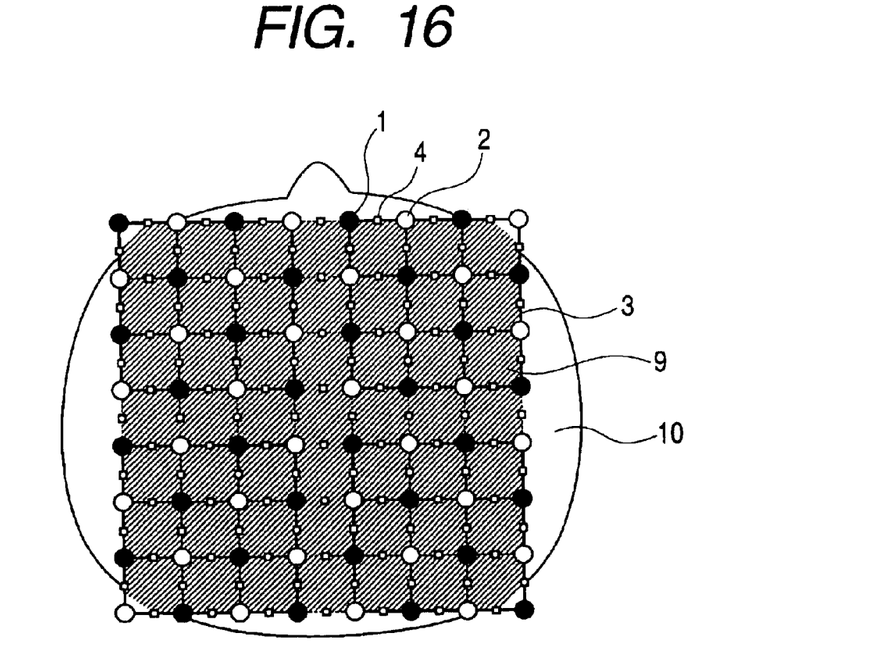
FIG. 16 is a view showing an optical topography image according to the embodiment using the probes shown in FIG. 6.

FIG. 16 is a view showing data obtained from measurement performed by using the probes in the arrangement of FIG. 6, which has been corrected as shown in FIG. 4 and displayed as an image. In this case, a head image 10 superimposed on a measurement image 9 is not a corrected image and a simplified head image is used. Sampling points 3 between irradiated points 1 and light receiving points 2 are arranged with about 21-mm spacings when the irradiation-to-detection distance is 30 mm. The measurement image 9 is an octagonal image occupying an area smaller than that of the shell 3. If there is a sampling point at which a quality signal could not be obtained by trouble or the like, it is possible to estimate the value at the sampling point at which the signal could not be obtained by using peripheral sampling points and thereby interpolate the image.

Figure 17:
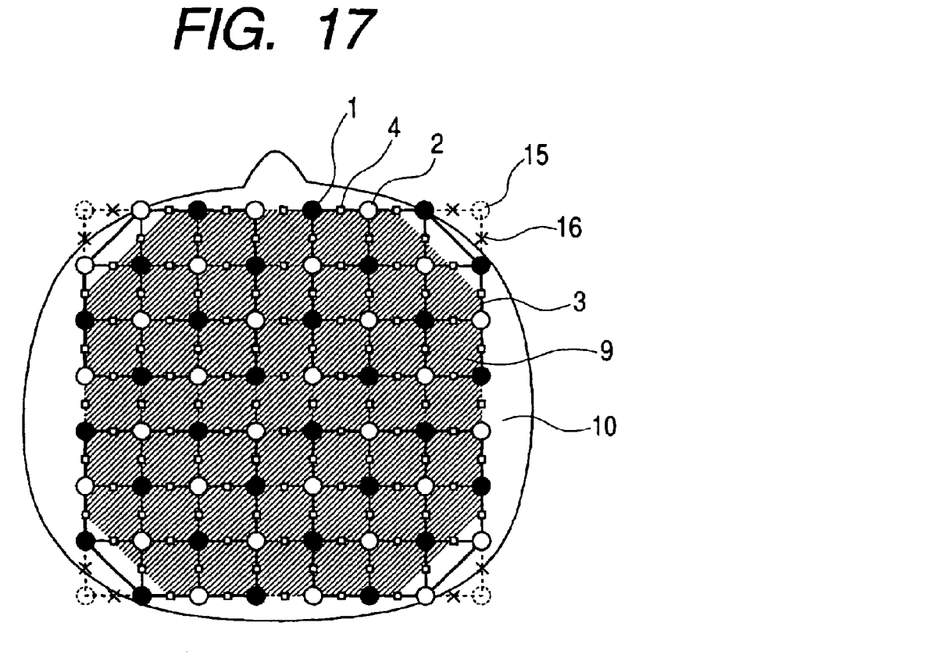
FIG. 17 is a view showing an optical topography image when different probes are used.

FIG. 17 shows a measurement image obtained as a result of making correction similar to that shown in FIG. 16 when one of the irradiation and light receiving points on each of the rhombic shells 3 is removed. Since sampling points 16 cannot be obtained around the removed points 15, the measurement image 9 has a configuration as shown in FIG. 17.

Figure 18:
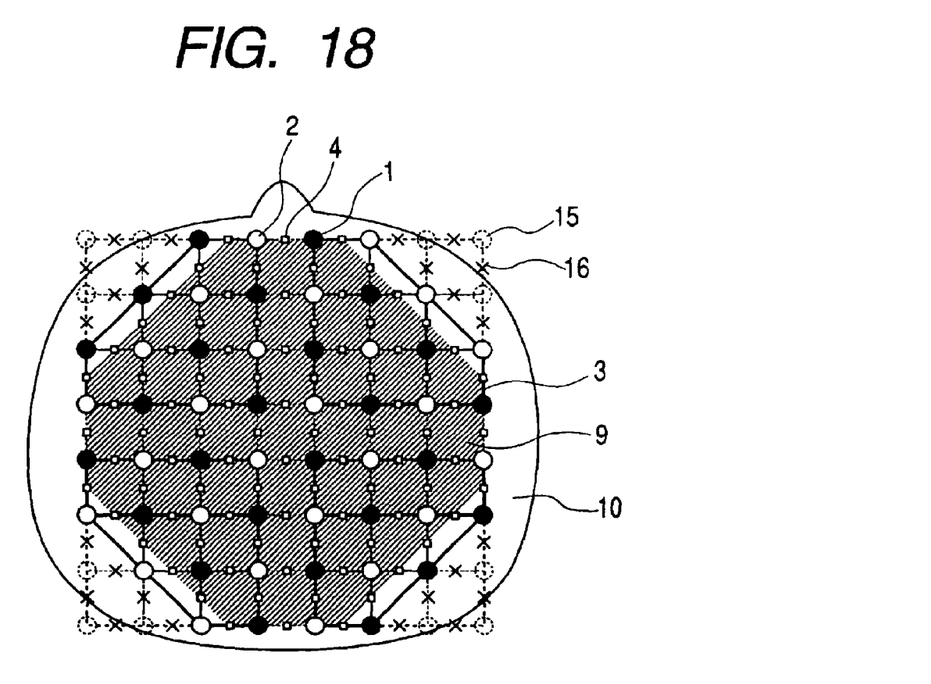
FIG. 18 is a view showing an optical topography image when other different probes are used.

FIG. 18 shows a measurement image obtained as a result of making correction similar to that shown in FIG. 16 when three of the irradiation and light receiving points on each of the rhombic shells 3 are removed.

Figure 19:
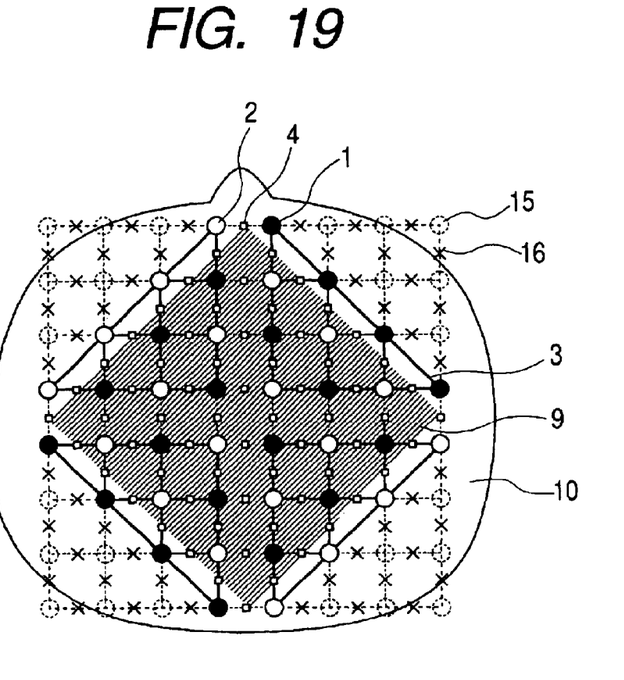
FIG. 19 is a view showing an optical topography image according to the embodiment using the probes shown in FIG. 8.

FIG. 19 shows a measurement image obtained as a result of making correction similar to that shown in FIG. 16 when six of the irradiation and light receiving points on each of the rhombic shells 3 are removed, i.e., when the probes in the arrangement of FIG. 8 are used.

Figure 20:
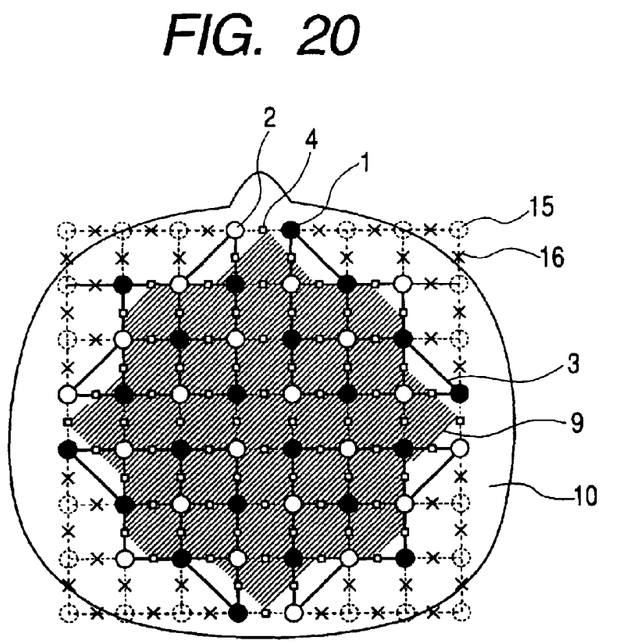
FIG. 20 is a view showing an optical topography image according to the embodiment using the probes shown in FIG. 7.

FIG. 20 shows a measurement image obtained as a result of making correction similar to that shown in FIG. 16 when five of the irradiation and light receiving points on each of the rhombic shells 3 are removed, i.e., when the probes in the arrangement of FIG. 7 are used.

Figure 21A:
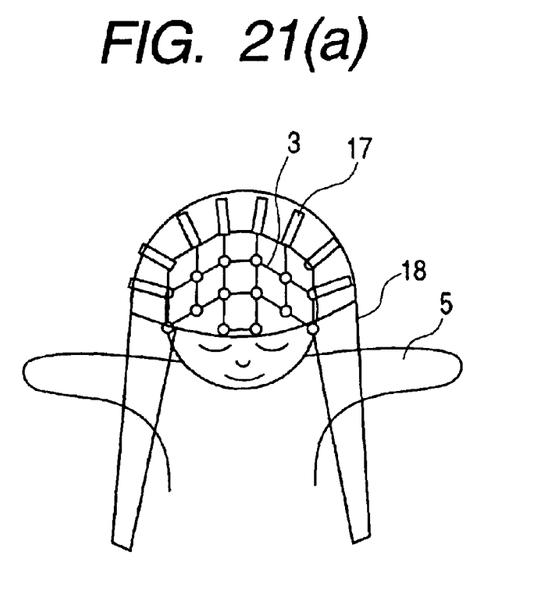
FIGS. 21A to 21C are views illustrating a method for fixing the probes according to each of the embodiments.
Figure 21B:
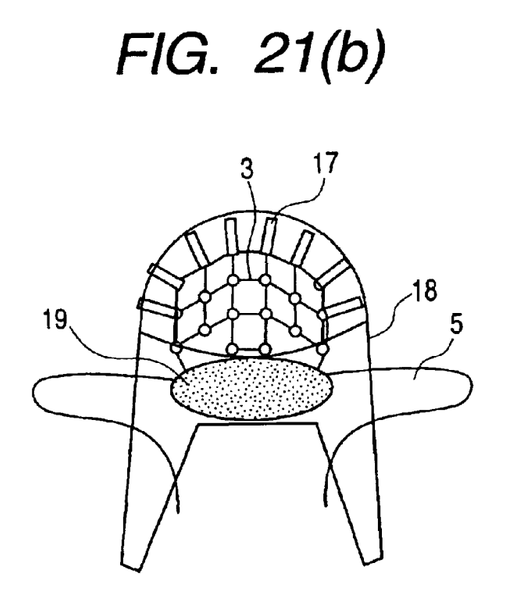
Figure 21C:
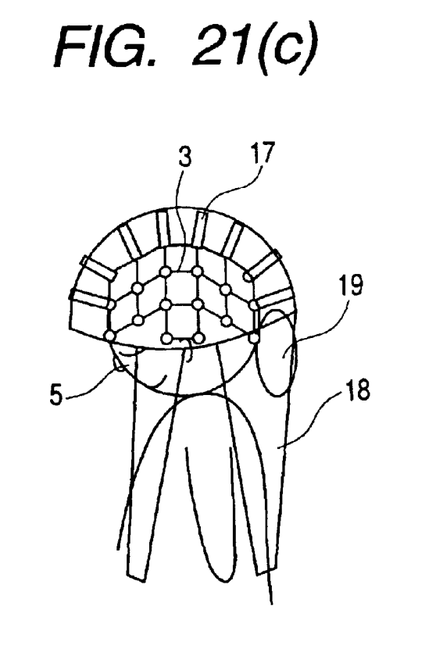

FIGS. 21A to 21C show an embodiment of a method for probe fixation when the probes according to the present invention are attached to a subject, of which FIG. 21A is a front view of the subject, FIG. 21B is a rear view thereof, and FIG. 21C is a side view thereof. Optical fiber fixing sockets 17 connected to the irradiated/light receiving points are attached onto the shells 3 such that optical fibers fitted in the optical fiber fixing sockets 17 are fixed thereby. The head of the subject is covered with a fixing cap 18 from over the optical fiber fixing sockets such that the probes as a whole do not fall down from the head. The cap 18 has strings which are tied under the chin, armpit, or the like for the fixation of the probes. It is possible to use an elastic material for the cap and fix the probes by using only the cap. It is also possible to trim the edge of the cap with rubber or a belt such that the cap is tight fitted for fixation. In these cases, however, tying or fastening should not be too tight such that fixation is not an annoyance to the subject. If measurement is performed with the subject in a recumbent posture, a pillow 19 may be placed appropriately near the neck of the subject to keep the head of the subject in a raised state and prevent a load on the fixing sockets 17. In this case, the pillow 19 has been attached to the cap but it may also be placed on a recumbent bed or fixed to the bed.

Figure 22:
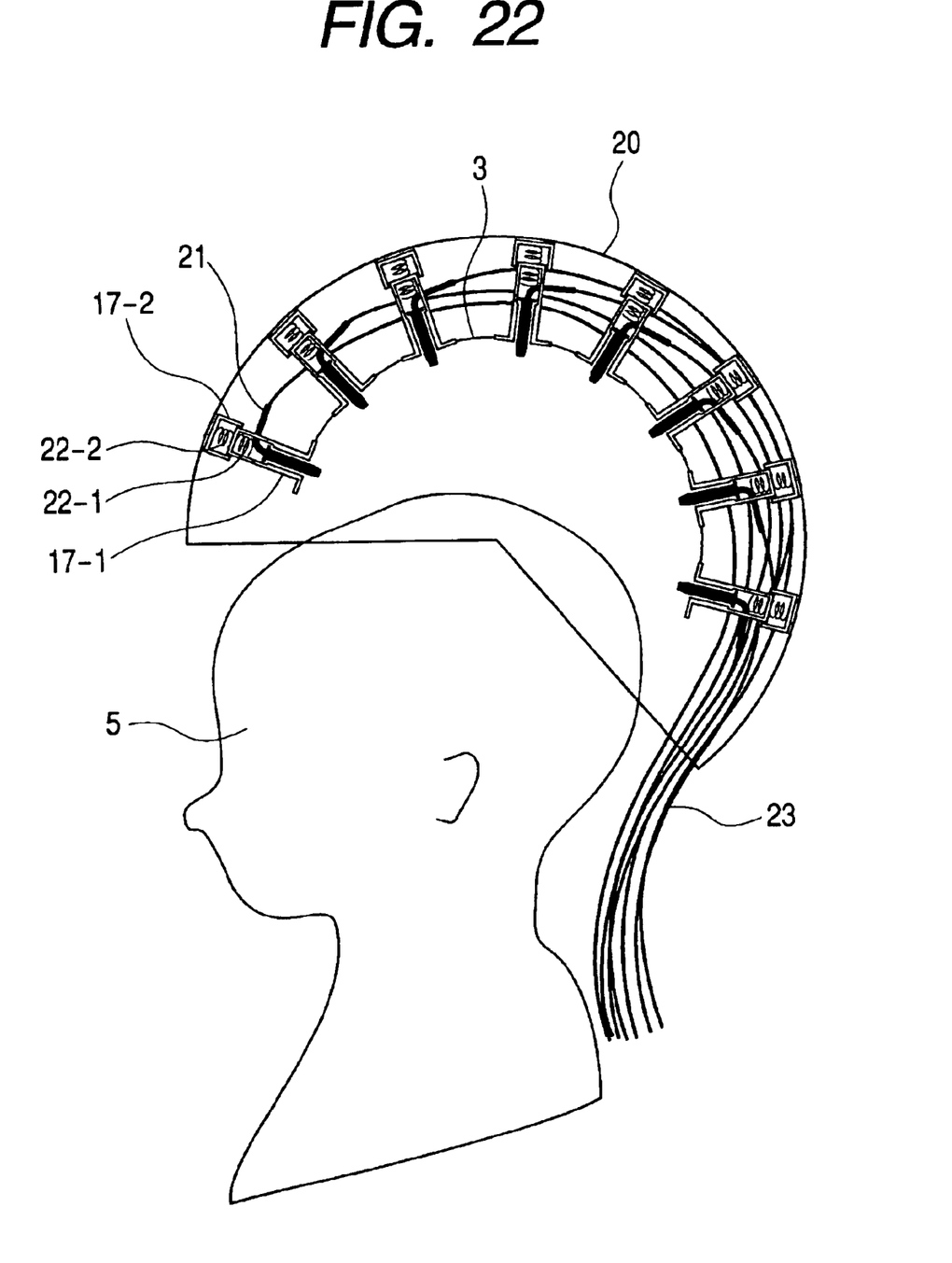
FIG. 22 is a view showing probes according to another embodiment.

FIG. 22 shows another embodiment of the method for probe fixation when the probes according to the present invention are attached to a subject. The probes are fixed in a helmet 20 and the subject wears the helmet 20 when measurement is performed. The lower parts 17-1 of optical fiber fixing sockets are attached to the shells 3 and optical fiber tip portions 21 are inserted therein. The lower parts 17-1 of optical fiber fixing sockets are internally provided with springs 22-1 such that the optical fiber tip portions 21 are vertically movable. Accordingly, the optical fiber tip portions 21 retract when the subject 5 puts on the helmet 20 so that they are less likely to cause pain in the subject 5. The lower parts 17-1 of optical fiber fixing sockets are inserted in upper parts 17-2 of optical fiber fixing sockets which are fixed in the helmet 20 so that the lower parts 17-1 of optical fiber fixing sockets are vertically movable with springs 22-2 provided in the upper parts 17-2 of the optical fiber fixing sockets. Since the shells 3 are deformed in conformity with the configuration of the head of the subject 5, the effects of enhancing the fittability of the shells to the head and reducing the probability of causing pain are achieved. Instead of the springs 22-1 or 22-2, another material or instrument functioning as a cushioning material or an elastic material or instrument may also be used. In that case, the upper parts 17-2 of optical fiber fixing sockets need not be used. Alternatively, the lower parts 17-1 of optical fiber fixing sockets need not be used. Optical fibers 23 extend from the optical fiber tip portions 21 through the space between the shells 3 and the helmet 20 to be extracted collectively from the end of the helmet 20 in the vicinity of the neck to the outside. Besides extracting the optical fibers 23 from the end of the helmet 20 to the outside, it is also possible to form a single or plurality of holes in a specified portion of the helmet and extract the optical fibers 23 therefrom to the outside. The space between the shells 3 and the helmet 20 may be hollow or filled with a cushioning material such as a gel, sponge, or the like. In that case, a path allowing the passage of the optical fibers 23 is provided.

The portions of the lower parts 17-1 of optical fiber fixing sockets which come in contact with the head may also be lined with a sponge or a gel-like cushioning material. This reduces stimulation to the scalp. It is also possible to impart conductivity to a cushioning material by impregnating sponge with a physiological saline or using a conductive gel material, connect electric lines to the cushioning material, and thereby use the conductive cushioning material as electrodes for electrical brain wave measurement. This allows optical measurement and electrical brain wave measurement to be performed simultaneously. Alternatively, the sockets and the electrodes may be disposed separately such that the electrodes for electrical brain wave measurement are positioned between the sockets.

Figure 23A:
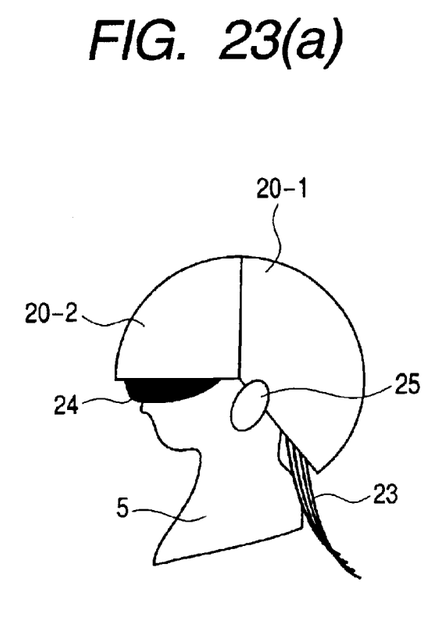
FIGS. 23A and 23B are views each showing probes according to still another embodiment.
Figure 23B:
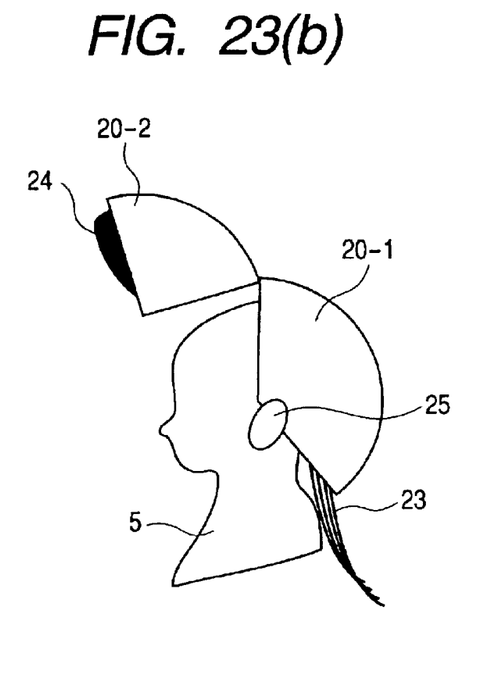

FIGS. 23A and 23B show a variation of probes configured as a helmet shown in FIG. 22. The helmet is composed of two structures of a helmet front part 20-2 and a helmet rear part 20-1 shown in FIG. 23A, which are connected to each other with hinges to be switchable between open and closed states. The probes are similarly constructed to those shown in FIG. 22 in that they have shells to which optical fibers are attached within each of the structures and the optical fibers and the shells are outwardly press-expandable in accordance with the size and configuration of the head. The probes are put on the subject 5 with the helmet front part 20-2 and the helmet rear part 20-1 shown in FIG. 23B being in the open state and worn by subsequently closing the helmet front part 20-2. It is possible to attach a monitor 24 configured as a sun visor or a pair of goggles to the helmet front part 202. The monitor 24 is used when brain activity is optically measured while visual information or visual stimulation is given to the subject. It is also possible to attach an earphone 25 to the helmet and perform measurement while giving audio information or auditory stimulation to the subject. The present variation allows easy wearing of the helmet by a subject who cannot put on the helmet by himself or herself, such as a new-born. The helmet may be divided not only into the front and rear parts but also into left and right parts or into three parts including a rear part, a front right part, and a front left part. The helmet may also be divided into three or more parts. For a subject who can put on the helmet by himself or herself, an integral-type helmet to be press-expandably put on, not a helmet divided in parts, may also be used.

Figure 24:
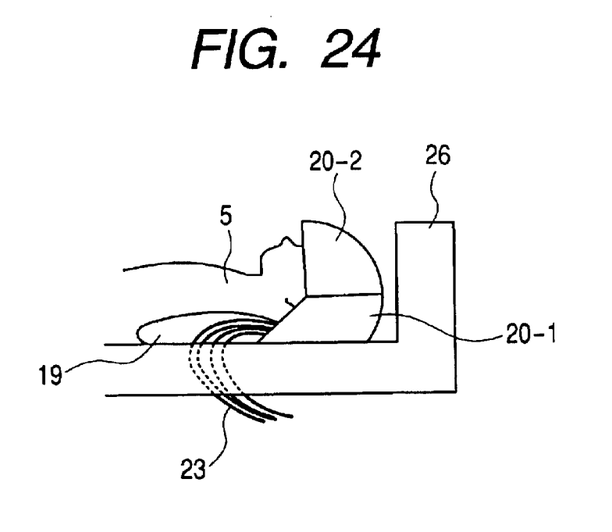
FIG. 24 is a view of the probes shown in FIG. 22 or 23 when they are used.

FIG. 24 shows the case where measurement is performed with a subject wearing the helmet-type probes shown in FIG. 22, FIG. 23A, or FIG. 23B in a recumbent posture. The helmet 20 is fixed onto a bed 26 or placed thereon. For the protection of the neck of the subject 5, a pillow 19 is fixed to the bed or to the helmet or placed on the bed 26. Optical fibers 23 extend through the bed 26 to be extracted to the outside such that they are prevented from being tucked under the subject 5. In this case, the optical fibers 23 are also allowed to extend through the pillow 19. This prevents the optical fibers from being tucked under the subject 5 or obstructing measurement.

The helmet may also be painted with a comfortable color, pattern, picture, or the like which relieves the tension of the subject or configured as a character such as an animal provided that it retains the function of probes.

What is claimed is:

1. An optical system for measuring a variation in a concentration of a metabolite or a variation in blood flow in a living body by using a plurality of light irradiators and a plurality of light detectors, the system comprising:

a probe to be attached to a head of a subject, the probe having an array of irradiating portions of said light irradiators and light receiving portions of said light detectors, the array including even partial arrays in each of which the irradiating portions and the light receiving portions are alternately arranged in a rhombic lattice configuration obtained by obliquely deforming a tetragonal lattice, the even partial arrays being arranged in a semispherical configuration to compose the array.

2. The optical system of claim 1, wherein a rhombus in each of the partial arrays has a variable apical angle.

3. The optical system of claim 1, wherein each of said partial arrays is held by a holding portion for holding said irradiating portions and said light receiving portions at lattice points of the rhombic lattice obtained by obliquely deforming a tetragonal lattice, the holding portion being composed of a plastic member.

4. The optical system of claim 3, wherein said holding portion includes a plurality of optical fiber fixing sockets for fixing respective optical fibers composing said irradiating portions and said light receiving portions and a coupling member for coupling said optical fiber sockets to each other and has a net-like structure.

5. The optical system of claim 1, wherein said partial arrays are arranged to have respective outer edges extending substantially in parallel with each other.

6. The optical system of claim 1, wherein said partial arrays are arranged to have respective outer edges spaced apart at a distance substantially equal to a distance between any one of the irradiating portions and the adjacent light receiving portion within each of the partial arrays and the respective irradiating portions and light receiving portions composing the adjacent partial arrays have positions thereof inverted.

7. An optical system for measuring a variation in a concentration of a metabolite or a variation in blood flow in a living body by using a plurality of light irradiators and a plurality of light detectors, the system comprising:

a probe to be attached to a head of a subject, the probe having an array of irradiating portions of said light irradiators and light receiving portions of said light detectors, the array including a rectangular partial array in which the irradiating portions and the light receiving portions are alternately arranged in a tetragonal lattice configuration and partial arrays in each of which the irradiating portions and the light receiving portions are alternately arranged in a rhombic lattice configuration obtained by obliquely deforming a tetragonal lattice, the partial arrays each in the rhombic lattice configuration being located on left and right sides of the rectangular partial array in the tetragonal lattice configuration to compose the array in conjunction with the rectangular partial array in the middle.

8. An optical system for measuring a variation in a concentration of a metabolite or a variation in blood flow in a living body by using a plurality of light irradiators and a plurality of light detectors, the system comprising:

a probe to be attached to a head of a subject, the probe including a first partial array in which irradiating portions of said light irradiators and light receiving portions of said light detectors are alternately arranged in a rhombic lattice configuration obtained by obliquely deforming a tetragonal lattice and a second partial array in which the irradiating portions of said light irradiators and the light receiving portions of said light detectors are alternately arranged in a tetragonal lattice configuration; and display means for displaying a signal distribution measured by using said probe, the display means displaying an arrangement of the signal distribution corresponding to said first partial array by correcting it into an arrangement in a tetragonal lattice configuration similar to an arrangement of the signal distribution corresponding to said second partial array.

* * * * *